(12) United States Patent
VanDiver et al.

(10) Patent No.: US 7,044,933 B2
(45) Date of Patent: May 16, 2006

(54) FLUID INJECTION SYSTEM FOR CORONARY INTERVENTION

(75) Inventors: Mark H. VanDiver, Argyle, NY (US); Colin P. Hart, Queensbury, NY (US); Kevin C. Martin, Stillwater, NY (US); Thomas R. Delcourt, Queensbury, NY (US); Eric Houde, Saratoga Springs, NY (US)

(73) Assignee: Scimed Life Systems, Inc., Maple Grove, MN (US)

( * ) Notice: Subject to any disclaimer, the term of this patent is extended or adjusted under 35 U.S.C. 154(b) by 305 days.

(21) Appl. No.: 09/796,779

(22) Filed: Mar. 1, 2001

(65) Prior Publication Data

US 2002/0123716 A1   Sep. 5, 2002

(51) Int. Cl.
  *A61M 1/00* (2006.01)
(52) U.S. Cl. ..................................... 604/151
(58) Field of Classification Search ................ 604/247, 604/65–67, 131, 132, 150–154; 600/432; 222/386; 128/DIG. 1, DIG. 12
See application file for complete search history.

(56) References Cited

U.S. PATENT DOCUMENTS

| | | | |
|---|---|---|---|
| 3,674,009 A | 7/1972 | Williamson | |
| 3,701,345 A | 10/1972 | Heilman et al. | |
| 3,812,843 A | 5/1974 | Wootten et al. | 128/2 R |
| 4,006,736 A * | 2/1977 | Kranys et al. | 600/432 |
| 4,024,864 A | 5/1977 | Davies et al. | |
| 4,085,749 A * | 4/1978 | Chambron | 604/143 |
| 4,250,887 A | 2/1981 | Dardik et al. | |
| 4,370,982 A | 2/1983 | Reilly | |
| 4,502,488 A | 3/1985 | Degironimo et al. | |
| 4,533,346 A | 8/1985 | Cosgrove, Jr. et al. | |
| 4,551,133 A | 11/1985 | Zegers de Beyl et al. | |
| 4,634,431 A | 1/1987 | Whitney et al. | |
| 4,695,271 A | 9/1987 | Goethel | |
| 4,767,406 A | 8/1988 | Wadham et al. | |
| 4,812,724 A | 3/1989 | Langer et al. | |
| 4,854,324 A | 8/1989 | Hirschman et al. | |
| 4,861,340 A | 8/1989 | Smith et al. | |
| 4,877,956 A | 10/1989 | Priest | |
| 4,919,650 A | 4/1990 | Feingold et al. | |
| 4,952,205 A | 8/1990 | Mauerer et al. | |

(Continued)

FOREIGN PATENT DOCUMENTS

EP   0 346 950 B2   9/1997

(Continued)

OTHER PUBLICATIONS

International Search Report; PCT/US01/23635 issued on Jun. 2, 2002.

*Primary Examiner*—Nicholas D. Lucchesi
*Assistant Examiner*—Matthew F. DeSanto
(74) *Attorney, Agent, or Firm*—Miller, Matthias & Hull (57) ABSTRACT

A fluid injection apparatus and method of injecting fluid are disclosed. The apparatus includes a control syringe electrically connected to a power-actuated syringe. A sensor is provided proximate the control syringe to monitor the position of the plunger therein, with a signal representative of plunger position then being communicated to a processor for calculation of a corresponding control signal. The control signal is received by an actuator of the power-actuated syringe to move the plunger of the power-actuated syringe in a manner related to movement of the control syringe. The control syringe is provided with a feedback device to provide the operator with an indication as to the pressure of the fluid being injected into a patient.

13 Claims, 6 Drawing Sheets

U.S. PATENT DOCUMENTS

| Patent | | Date | Inventor | Ref |
|---|---|---|---|---|
| 5,014,715 | A | 5/1991 | Chapolini | |
| 5,034,004 | A | 7/1991 | Crankshaw | 604/154 |
| 5,053,002 | A * | 10/1991 | Barlow | 604/30 |
| 5,137,514 | A | 8/1992 | Ryan | |
| 5,139,484 | A | 8/1992 | Hazon et al. | |
| 5,232,449 | A | 8/1993 | Stern et al. | 604/154 |
| 5,236,416 | A | 8/1993 | McDaniel et al. | |
| 5,300,029 | A | 4/1994 | Denance | 604/117 |
| 5,322,511 | A | 6/1994 | Armbruster et al. | |
| 5,515,851 | A | 5/1996 | Goldstein | |
| 5,562,614 | A | 10/1996 | O'Donnell | |
| 5,569,208 | A * | 10/1996 | Woelpper et al. | 604/183 |
| 5,573,515 | A * | 11/1996 | Wilson et al. | 604/236 |
| 5,611,784 | A | 3/1997 | Barresi et al. | |
| 5,662,612 | A | 9/1997 | Niehoff | 604/155 |
| 5,697,899 | A | 12/1997 | Hillman et al. | |
| 5,733,259 | A | 3/1998 | Valcke et al. | |
| 5,792,102 | A * | 8/1998 | Muller-Spath | 604/70 |
| 5,800,397 | A | 9/1998 | Wilson et al. | |
| 5,830,194 | A | 11/1998 | Anwar et al. | |
| 5,840,026 | A * | 11/1998 | Uber et al. | 600/431 |
| 5,842,468 | A | 12/1998 | Denyer et al. | |
| D404,717 | S | 1/1999 | Duchon et al. | |
| 5,865,805 | A | 2/1999 | Ziembra | |
| 5,868,710 | A | 2/1999 | Battiato et al. | |
| 5,879,627 | A | 3/1999 | Tanihata | |
| 5,882,343 | A | 3/1999 | Wilson et al. | |
| 5,913,844 | A | 6/1999 | Ziembra et al. | |
| 5,916,165 | A | 6/1999 | Duchon et al. | |
| 5,925,022 | A | 7/1999 | Battiato et al. | 604/208 |
| 5,928,197 | A | 7/1999 | Niehoff | 604/155 |
| 5,988,587 | A | 11/1999 | Duchon et al. | |
| 6,030,368 | A | 2/2000 | Anwar et al. | |
| 6,099,502 | A | 8/2000 | Duchon et al. | |
| 6,171,276 | B1 | 1/2001 | Lippe et al. | |
| 6,221,045 | B1 | 4/2001 | Duchon et al. | |

FOREIGN PATENT DOCUMENTS

| | | |
|---|---|---|
| FR | 2 757 772 | 7/1998 |
| FR | 2757772 A1 * | 7/1998 |
| WO | WO 99/24094 | 5/1999 |
| WO | WO 99/24095 | 5/1999 |

* cited by examiner

FLUID INJECTION SYSTEM FOR CORONARY INTERVENTION

FIELD OF THE INVENTION

The invention generally relates to fluid dispensing apparatus and, more particularly, relates to apparatus for dispensing fluid in a controlled manner for use in medical procedures.

BACKGROUND OF THE INVENTION

Angiography is a procedure used in the detection and treatment of abnormalities or restrictions in blood vessels. During angiography, a radiographic image of a vascular structure is obtained by injecting radiographic contrast material through a catheter into a vein or artery. Vascular structure fluidically connected with the vein or artery in which the injection occurs is filled with contrast material. X-rays are then passed through the region of the body in which the contrast material was injected, with the x-rays being absorbed by the contrast material, creating a radiographic outline or image of the blood vessel containing the contrast material. The x-ray image of the blood vessels filled with the contrast material is usually recorded onto film or videotape and then displayed on a fluoroscope monitor.

During angiography, after a physician places a catheter into a vein or artery, the angiography catheter is connected to either a manual or automatic contrast injection mechanism. With a typical manual contrast injection mechanism, a syringe and catheter combination are used wherein the user depresses the plunger of the syringe to inject the contrast. Such a method allows the user to feel the resistance to injection so that he or she can adjust pressure accordingly.

Given the relatively small diameter of the catheter and the potentially viscous nature of the contrast, the injection of such material can often be difficult to perform manually. This is especially true when quick injection is required. Consequently, automatic contrast injection mechanisms have been devised. Such mechanisms use a power-actuator to drive the plunger of a syringe. Examples of such automatic machines are disclosed in U.S. Pat. Nos. 5,515,851 and 5,916,165.

However, while a power-actuated plunger is employed with such devices, the user is provided with no indication as to the resistance encountered by the fluid being injected. In both devices, touch pads or buttons are provided which, upon depression, cause the injection of the fluid to be initiated. Removal of pressure from the actuation buttons causes the injection process to be stopped. Not only is the user provided with no feedback as to the resistance encountered by the fluid being injected with such devices, but the control apparatus of such devices is of a foreign nature to most clinicians. Most clinicians are normally used to the operation of a syringe type mechanism, wherein the plunger of the syringe becomes more difficult to depress as output pressure increases.

SUMMARY OF THE INVENTION

In accordance with one aspect of the invention, an injection apparatus is provided which comprises a control syringe, a power syringe, a processor, a sensor, and a feedback device. The control syringe includes a manually movable plunger and the power syringe includes a power-actuated plunger. The sensor is operatively associated with the control syringe and transmits a signal representative of control syringe plunger position to the processor. The processor generates a control signal based on the position signal and transmits the control signal for movement of the power-actuated plunger. The feedback device is in communication with the power syringe and the control syringe and affects the force required to manually move the plunger of the control syringe.

In accordance with another aspect of the invention, a method of injecting fluid is provided, which comprises the steps of manually depressing a plunger of a control syringe, moving a plunger of a power-operated syringe in sequence with the control syringe plunger, and providing tactile feedback to a user of the control syringe. Movement of the power-actuated plunger increases fluid pressure within a conduit connected to an output of the power-actuated syringe. The level of tactile feedback is related to the fluid pressure within the output conduit.

In accordance with another aspect of the invention, an injection apparatus is provided which comprises a power-actuated output device adapted to inject fluid into a patient, an input device manipulable by a user, a controller adapted to move the power-actuated output device in accordance with the input device, and a feedback device adapted to provide the user with an indication as to the pressure of the fluid being injected by the power-actuated output device.

In accordance with another aspect of the invention, an injection apparatus is provided which comprises a control syringe, a power syringe, a processor, and a sensor. The control syringe includes a manually movable plunger and the power syringe includes a power-actuated plunger. The sensor is operatively associated with the control syringe and transmits a signal representative of control syringe plunger position to the processor. The processor generates a control signal based on the position signal and transmits the control signal for movement of the power actuated plunger.

In accordance with another aspect of the invention, a method of injecting fluid is provided which comprises the steps of manually operating an input device, and moving a power-actuated output device in sequence with the input device, movement of the power-actuated output device increasing fluid pressure within a conduit connected to an output of the power-actuated output device and injecting fluid contained therein.

These and other aspects and features of the present invention will become more apparent from the following detailed description when taken in conjunction with the accompanying drawings.

While the invention is susceptible to various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions and equivalents falling within the spirit and scope of the invention as defined by the appended claims.

DETAILED DESCRIPTION OF THE PREFERRED EMBODIMENTS

Figure 1:
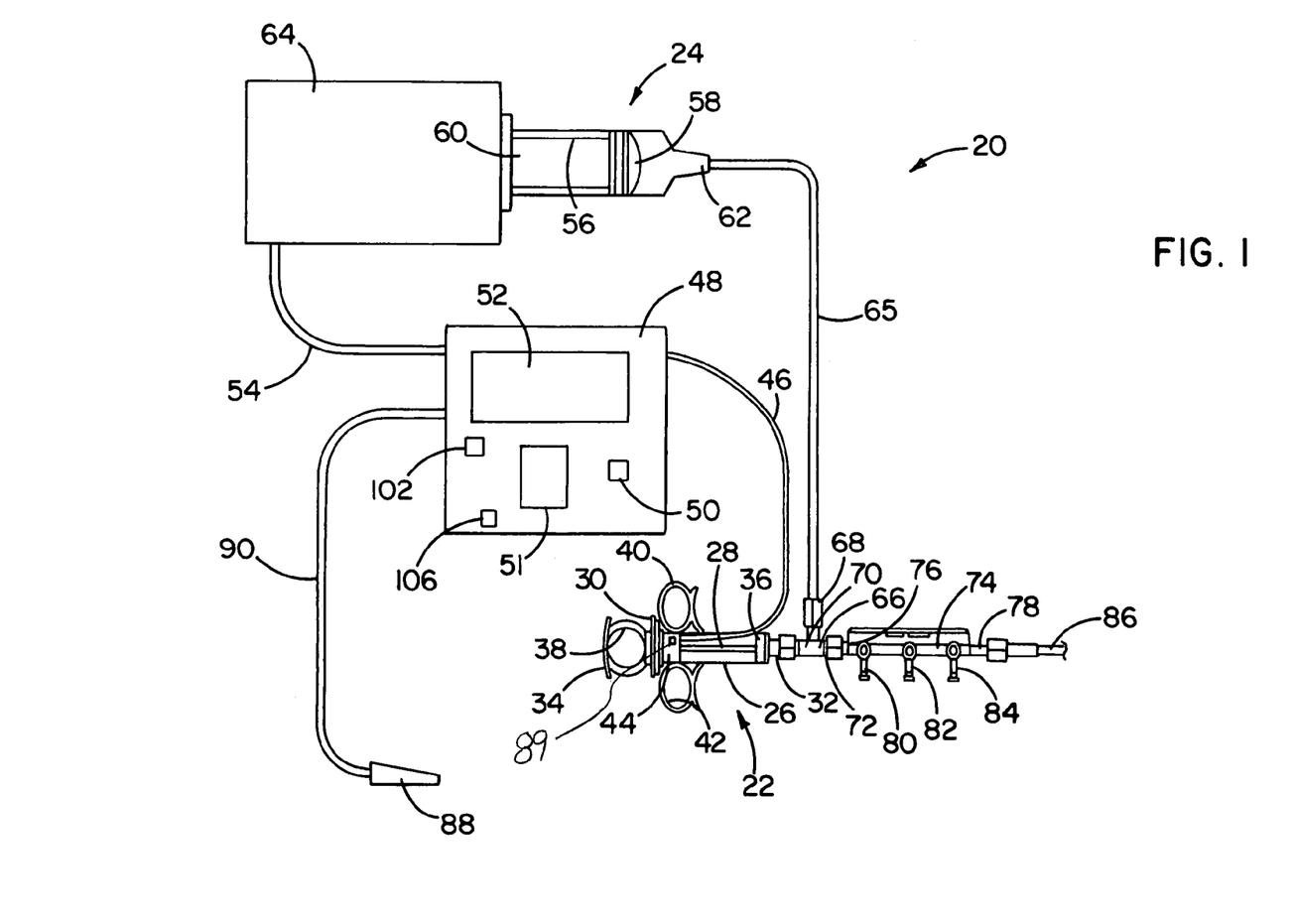
FIG. 1 is a schematic representation of a fluid injection apparatus constructed in accordance with the teachings of the invention.

Referring now to the drawings, and with specific reference to FIG. 1, a fluid injection apparatus constructed in accordance with the teachings of the invention is generally depicted by reference numeral 20. While the apparatus 20 is generally described in conjunction with the injection of contrast for use in angiography procedures, it is to be understood that the teachings of the invention can be employed in other applications and for the injection of other fluids as well.

The apparatus 20 includes a control or input device 22 and a power-actuated device such as a syringe 24. Movement of the power-syringe 24 is entirely controlled by movement of the input device 22 in a mimicking relationship. While the control device 22 is depicted to be provided in a form of a conventional syringe, it is to be understood that the teachings of the invention can be employed using other forms of input devices 22 including, but not limited to, joy sticks, slide bars, accelerator pads, push buttons, and the like. Moreover, the control device 22 need not be operated by hand, but could also include devices operated by other input including, but not limited to, foot actuation, head movements, eye movements, voice recognition, and the like.

Figure 3:
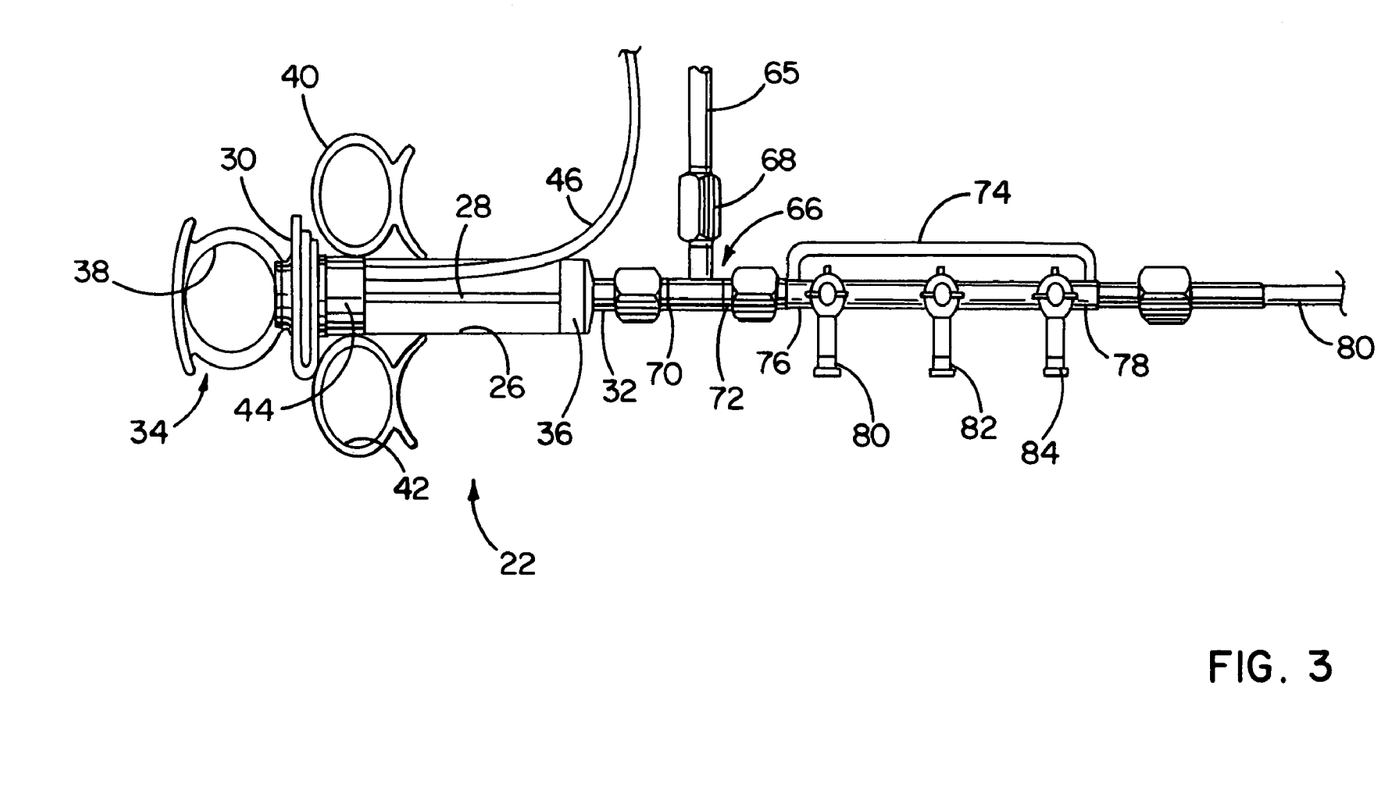
FIG. 3 is an enlarged side view of a control syringe constructed in accordance with the invention.

As depicted best in FIG. 3, the control device 22 includes a syringe cylinder 26 in which a plunger 28 is slidably disposed. The cylinder 26 includes an open end 30 and a reduced diameter output end 32. The plunger 28 includes an actuator end 34 and a working end 36. The actuator end 34 may be provided in the form of a ring 38 shaped to accommodate the thumb of a user, with corresponding first and second finger rings 40, 42 being provided in a conventional manner on the cylinder 26.

Also shown in FIG. 3 is a sensor 44 proximate the plunger 28. The sensor 44 is provided to monitor the position of the plunger 28 and generate a signal 46 representative of the location or movement of the plunger 28 relative to the cylinder 26. In the depicted embodiment, the sensor 44 is provided in the form of a linear voltage differential transmitter (LVDT), but can be provided in the form of any other conventional type of position or displacement sensor including, but not limited to, encoders, variable resistance devices, resolvers, magnetically readable devices, as well as infrared and other visually readable devices.

The signal 46 is received by an operator interface module 48. The operator interface module 48 includes a processor 50, an input device such as a keypad 51, as well as a monitor or display 52. As will be described in further detail herein, the processor 50 of the operator interface module 48 receives the position signal 46 and generates a control signal 54 communicated to the power-actuated syringe 24.

The power-actuated syringe 24 includes a cylinder 56 having a plunger 58 slidably disposed therein. The cylinder 56 includes an open end 60 as well as a reduced diameter output end 62. Proximate the open end 60 is an actuator 64 for driving the plunger 58 through the cylinder 56. The actuator 64 may be provided in a number of forms including, but not limited to, motor-driven drive trains, hydraulic rams, pneumatic systems, and the like. The volume of the power-actuated syringe 24 is greater than that of the control device 22. In one embodiment this is accomplished by providing the cylinder 56 of the power actuated syringe 24 with a larger diameter than the cylinder 26 of the control syringe 22.

The output end 62 of the power syringe 24 is connected to a fluid line 65 terminating in a tee-fitting 66 having an input 68, a first output 70, and a second output 72, as shown best in FIG. 3. It can accordingly be seen that the fluid output from the power syringe 24 is in fluid communication with the output end 32 of the control syringe 22. Downstream from the second output 72 of the tee-fitting 66 is a manifold 74 having an apparatus input end 76, an output 78, and a plurality of fluid input ports 80, 82, and 84.

While not depicted, the input ports 80, 82, 84, are provided for connection to a variety of different types of fluids for injection into a patient (not shown). More specifically, the input ports 80, 82, 84 may be connected to various types of contrast materials for use in conjunction with an angiographic procedure. In addition, one of the input ports 80, 82, 84 could be provided for connection to a saline solution for flushing the system after each use.

A catheter 86 is connected to the output 78 of the manifold 74. Completing the structure depicted in FIG. 1, a foot switch 88 is connected to the operator interface module 48 via a cable 90. It is to be understood that the cable 90 could be replaced with a wireless communication system wherein the foot switch 88, or other type of switch such as a switch 89 on the control syringe 22, can be provided with a transmitting device for communicating an actuation signal to a receiver of the operator interface module 48. It is to be further understood that wireless technology can be used in conjunction with the transmission of the position signal 46, the control signal 54 and any other signals associated with the apparatus 20. Moreover, the switch 88 can be provided directly on the control device 22.

Figure 2:
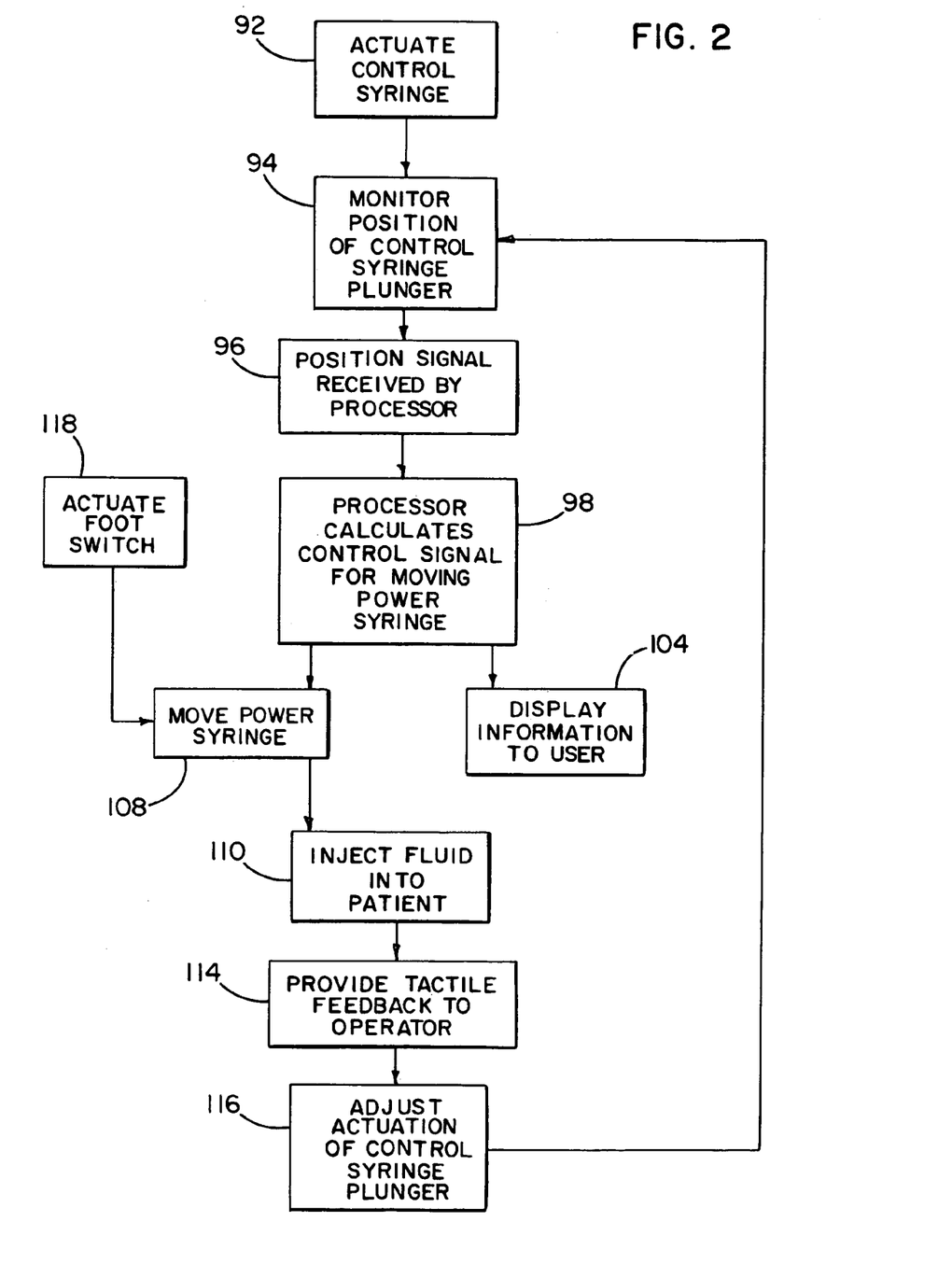
FIG. 2 is a flow chart depicting a sequence of steps which may be taken by a fluid injection apparatus constructed in accordance with the teachings of the invention.

Turning now to FIG. 2, a sample sequence of steps which may be taken by the system 20 is depicted in flow chart format. As indicated therein, the process is initiated by a user depressing the plunger 28 of the control syringe 22, as indicated by step 92. As indicated above, if other types of input or control devices 22 are provided, the system may be initiated by movement of other types of apparatus.

Once the plunger 28 of the control syringe 22 is depressed by a user, the position sensor 44 monitors such movement and generates the position signal 46, as indicated by step 94. The position signal 46 is received by the processor 50, as indicated by step 96, which in turn calculates the control signal 54, as indicated by step 98. Depending upon the algorithm employed by the processor 50, the control signal 54 will necessarily vary. In one embodiment, the control signal 54 may be a finite multiple of the position signal 46. Such proportional use of the position signal 46 can be adjustable. In other words, the gain employed by the processor 50 can be changed through appropriate manipulation by the user. For example, the operator interface module 48 may use the keypad 51 to dynamically change the gain.

In another embodiment, a number of different gains may be stored in a memory 102 of the operator interface module 48. Depending upon the operator using the apparatus 20, or the type of fluid being injected by the apparatus 20, the gain can be selected which is most suitable to the particular parameters of the use.

In a still further embodiment, the amount of fluid injected by the apparatus 20 per stroke of the plunger 28 of the control syringe 22 can be adjusted or selected from a number of different values stored in the memory 102. The display 52 may be employed to provide such information to the user of the apparatus 20, as indicated by step 104. The operator interface module 48 may further include a counter 106 to track the volume of fluid injected by the system 20.

The control signal 54 is communicated by the operator interface module 48 to the power-actuated syringe 24. The actuator 64 of the power syringe 24 employs the control signal 54 to move the plunger accordingly, as indicated by step 108. Fluid is then caused to be injected from output 78 through catheter 86 and into the patient, as indicated by step 110.

Not only is the fluid injected to the patient, but the operator of the apparatus 20 is provided with a feedback which, in the depicted embodiment, is provided in the form of a tactile feedback, as indicated by step 114. Since the output end 62 of the power syringe 24 is connected via tee-fitting 66 and first output 70 to the control syringe 22, the pressure of the fluid within the control device 22 is increased as the pressure within the fluid expelled by the power syringe 24 increases. In addition, as the pressure of the fluid injected into the patient increases, the pressure felt by the operator of the control device 22 also increases. Since the fluid within the catheter 86, the power syringe 24 and control syringe 22 are all in fluid communication, the increases or decreases within the pressure are communicated to the operator of the control device 22 in the form of tactile feedback.

This is advantageous in that the users of the system 20 are most likely to be familiar with the operation of manual syringes, and thus be acquainted with increases in the pressure of the fluid being injected. The operator can therefore adjust movement of the plunger 28 accordingly as indicated by a step 116. For example, an increase in the pressure may be an indication of the presence of a lesion or the like in the vascular structure in which the fluid is being injected. Such a tactile feedback will therefore provide the operator with valuable information for adjusting the angiographic procedure accordingly.

FIG. 2 also depicts a step 118 wherein the foot switch 88 is actuated to move the power plunger 58 as indicated by step 110. Such an operation may be advantageously employed at the beginning of angiographic procedure to, for example, check the location of the catheter 86 as it is being placed. The actuation of the foot switch 88, or other type of switch or actuator such as a linear actuator, joystick, or the like, would result in a small "puff" injection of the fluid such that the location of the contrast, and the location of the catheter 86, can be precisely determined. Alternatively, such a switch 88 could be used in a ventriculogram or other procedure requiring a quick injection of a relatively large volume of contrast.

Figure 4:
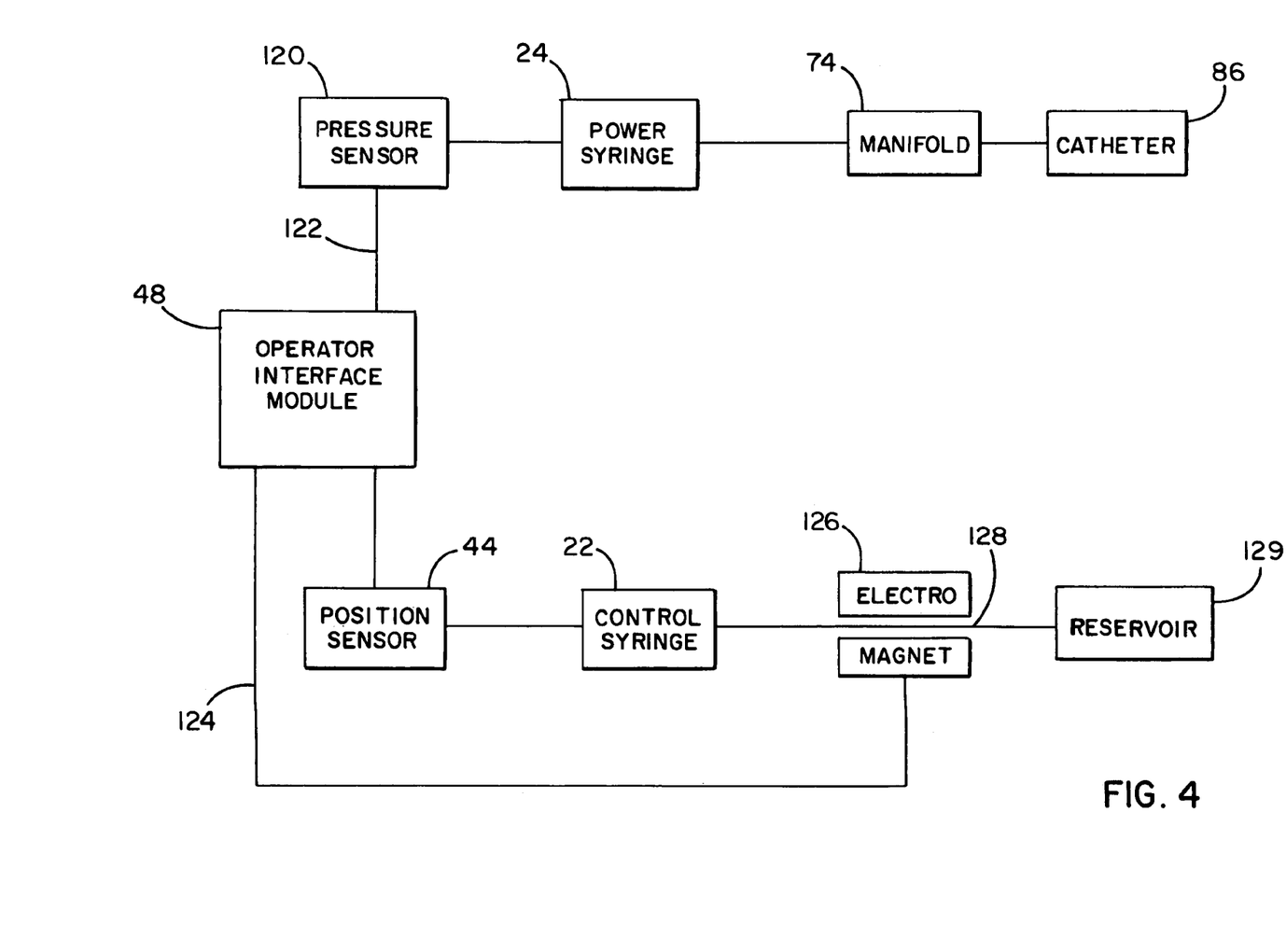
FIG. 4 is a block diagram of a second embodiment of a fluid injection apparatus constructed in accordance with the teachings of the invention.
Figure 5:
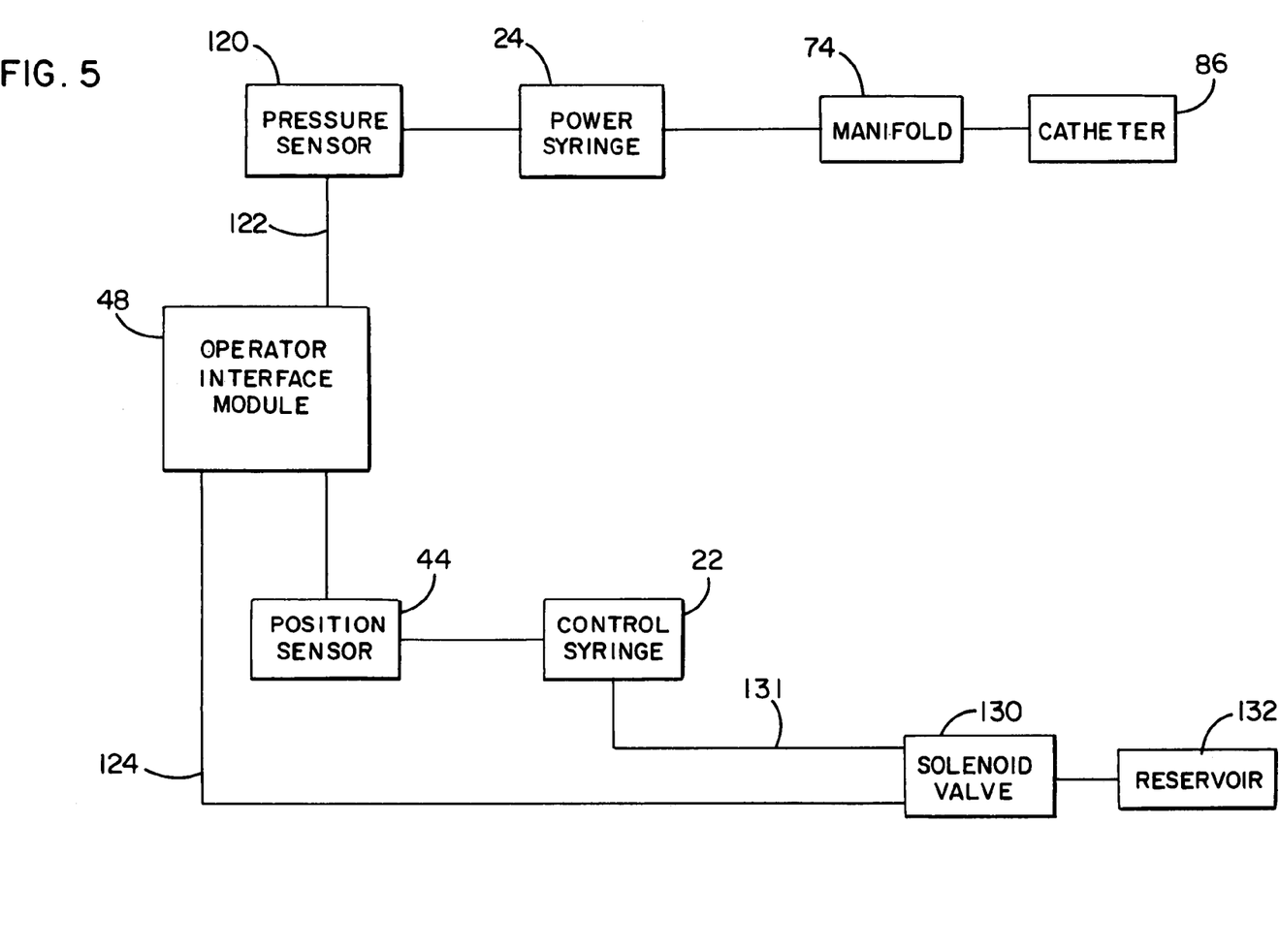
FIG. 5 is a block diagram of a third embodiment of a fluid injection apparatus constructed in accordance with the teachings of the invention.
Figure 6:
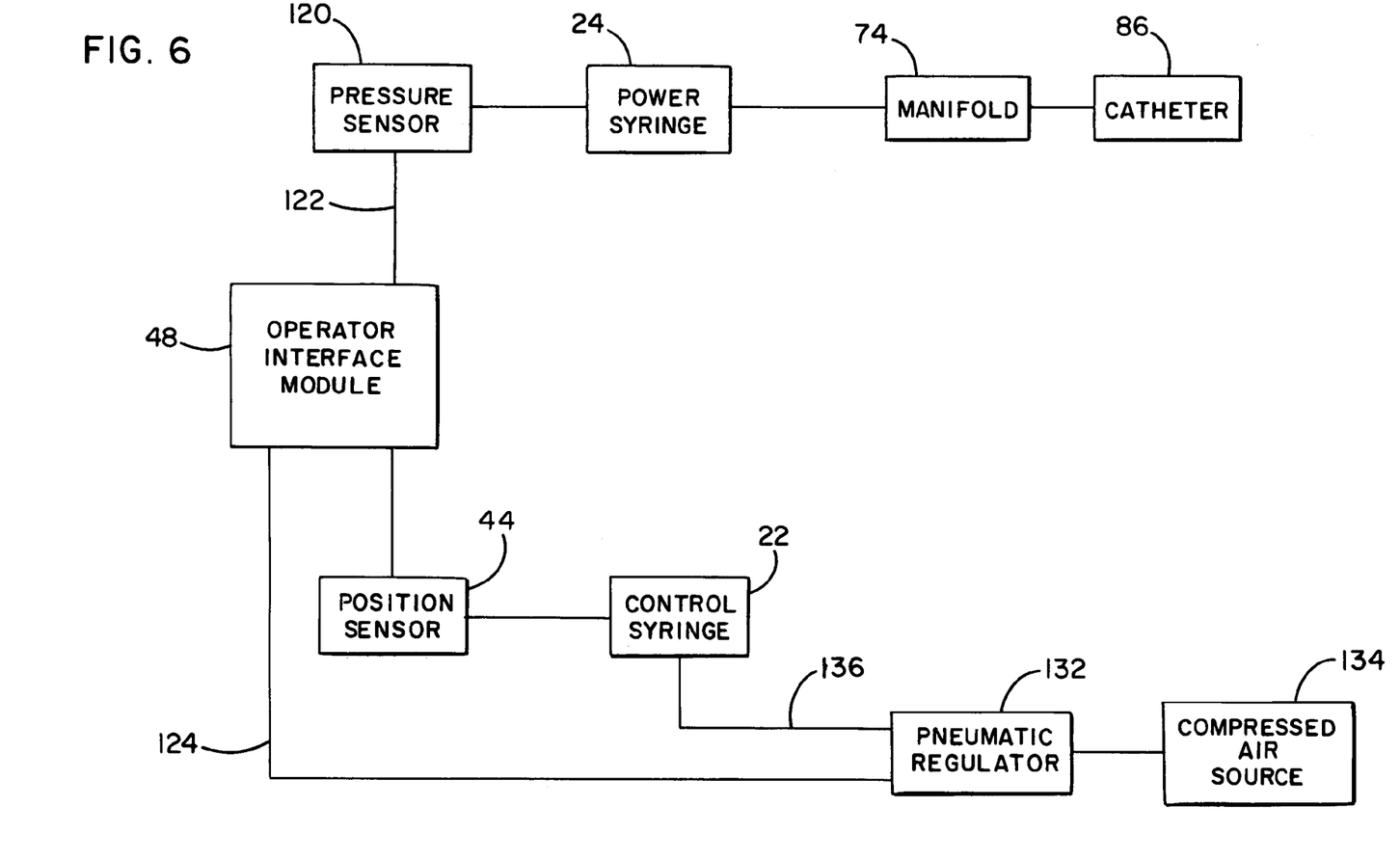
FIG. 6 is a block diagram of a fourth embodiment of a fluid injection apparatus constructed in accordance with the teachings of the invention.

In the alternative embodiments of FIGS. 4–6, the feedback need not be provided in the form of fluid communicated back to the control device 22 from the power syringe 24, but can be provided in alternative forms. For example, an alternative to fluid pressure generated tactile feedback is a force generated by electromagnets as shown in FIG. 4. Wherein like elements are employed in the alternative embodiments, like reference numerals are used.

In the second embodiment, a pressure sensor 120 is provided to monitor the pressure of the fluid being expelled by the power actuated syringe 54. The sensor 120 generates a pressure signal 122 which is communicated to the operator interface module 48 for generation of a feedback signal 124. The feedback signal 124 is utilized to increase or decrease the force required to depress the control syringe 22.

In the embodiment of FIG. 4, the feedback signal 124 is provided to actuate the electromagnets 126 provided proximate a fluid line 128 extending from the control syringe 22. The fluid line 128 is filled with a magnetic fluid such that upon actuation of the electromagnets 126, the viscosity of the magnetic fluid increases. Accordingly, the force required to depress the control syringe 22 increases as the viscosity of the magnetic fluid increases. The feedback signal need not be binary, but rather can be varied to thereby increase or decrease the force of the magnetic field generated by the electromagnets. The magnetic fluid may be reusable if a control syringe 22 is filled with a disposable fluid such as water and a separator plunger or the like is used to transfer pressure from the disposable fluid to the magnetic fluid.

In the embodiment of FIG. 5, the feedback signal may be utilized by a solenoid flow control valve 130. As shown therein, a fluid line 131 extends from the control syringe 22 to the solenoid flow control valve 130 and to a fluid reservoir 132. The feedback signal may be utilized to constrict the fluid line by appropriate positioning of the solenoid flow control valve 130. Constriction of the fluid line necessarily increases the force required to force fluid therethrough and thus increase the force required to actuate the control syringe 22.

In the embodiment of FIG. 6, the feedback signal may be utilized by a pneumatic regulator 133. The pneumatic regulator 133 may be connected to a source of compressed air 134 and be utilized to increase or decrease the air pressure within fluid line 136 extending from the control syringe 22.

Not only would such indirect feedback mechanisms be possible, but they would also enable the level of feedback to be tailored in a variety of ways. For example, a change in feedback force per unit of pressure could be greater at lower pressures for enhanced feel. As the pressure increases, the change in feedback force per unit of pressure could taper off so that the maximum pressure exerted by the feedback force would stay within reasonable levels for hand-held control syringes. Alternatively, the feedback could be tuned so that, for example, all sizes of catheters would feel similar to the operator. In other words, the injection of x cc's per second through a four French catheter could be made to feel the same to the operator as the same injection through a seven French catheter.

From the foregoing, it can be appreciated that the invention provides a fluid injection apparatus and method of injecting fluid which not only enables greater pressures to be generated than can normally be manually produced, but also provides an operator with feedback as to the pressure in the fluid being injected into a patient.

What is claimed is:

1. An injection apparatus, comprising:
   a control syringe including a manually movable plunger;
   a power syringe including a power-actuated plunger;
   a processor;
   a sensor operatively associated with the control syringe and transmitting a signal representative of control syringe plunger position to the processor, the processor generating a control signal based on the position signal and transmitting the control signal for movement of the power-actuated plunger; and
   a feedback device in communication with the power syringe and the control syringe, the feedback device affecting the force required to manually move the plunger of the control syringe, the feedback device including an electromagnet disposed adjacent a fluid line extending from the control syringe, the fluid line being filled with magnetic fluid, the electromagnet receiving the pressure signal and generating an magnetic field, the magnetic field constricting flow of the magnetic fluid within the fluid line based on the pressure signal to provide a user holding the control syringe with tactile feedback.

2. The injection apparatus of claim 1, further including a switch, wherein the switch is adapted to generate a signal to actuate the power-operated plunger independently of the control syringe.

3. The injection apparatus of claim 2, wherein the switch includes a foot pedal.

4. The injection apparatus of claim 2, wherein the switch is provided on the control syringe.

5. The injection apparatus of claim 1, further including a manifold disposed between the catheter and the output of the power syringe, the manifold including a plurality of inlets adapted to be placed in communication with injection fluids.

6. The injection apparatus of claim 5, wherein the feedback device includes a tee fitting having an inlet and first and second outlets, the inlet being connected to the power syringe, the first outlet being connected to an inlet of the manifold, the second outlet being connected to the outlet of the control syringe.

7. The injection apparatus of claim 1, including an operator interface module, the processor forming a part of the operator interface module.

8. The injection apparatus of claim 7, wherein the operator interface module includes a counter adapted to track total injection volume.

9. The injection apparatus of claim 1, wherein the power syringe includes an output connected to a catheter.

10. The injection apparatus of claim 1, wherein the sensor of claim 1 is a linear position sensor.

11. The injection apparatus of claim 1, wherein the control syringe includes a cylinder having a smaller diameter than a cylinder of the power syringe.

12. The injection apparatus of claim 1, wherein the operator interface module is adapted to us an algorithm in generating the control signal, the algorithm including an adjustable parameter corresponding to injection volume ejected from the power syringe per stroke of the control syringe plunger.

13. The injection apparatus of claim 1, wherein the feedback device includes a pressure sensor operatively associated with the power syringe, the pressure sensor generating a signal indicative of fluid pressure expelled by the power syringe.

* * * * *

UNITED STATES PATENT AND TRADEMARK OFFICE
CERTIFICATE OF CORRECTION

| | | |
|---|---|---|
| PATENT NO. | : 7,044,933 B2 | Page 1 of 1 |
| APPLICATION NO. | : 09/796779 | |
| DATED | : May 16, 2006 | |
| INVENTOR(S) | : VanDiver et al. | |

It is certified that error appears in the above-identified patent and that said Letters Patent is hereby corrected as shown below:

In column 8, claim 12, line 15, please delete "to us an algorithm," and insert -- to use an algorithm--.

Signed and Sealed this

Thirty-first Day of July, 2007

JON W. DUDAS
*Director of the United States Patent and Trademark Office*